US009808077B2

(12) United States Patent
Noble et al.

(10) Patent No.: US 9,808,077 B2
(45) Date of Patent: Nov. 7, 2017

(54) TOOTHBRUSH SYSTEM UTILIZING ORAL CARE CAPSULE

(71) Applicant: NOBLE INNOVATIONS LLC, Chapel Hill, NC (US)

(72) Inventors: Lise W. Noble, Chapel Hill, NC (US); Patrick T. Noble, Chapel Hill, NC (US)

(73) Assignee: Noble Innovations LLC, Chapel Hill, NC (US)

( * ) Notice: Subject to any disclaimer, the term of this patent is extended or adjusted under 35 U.S.C. 154(b) by 85 days.

(21) Appl. No.: 14/535,442

(22) Filed: Nov. 7, 2014

(65) Prior Publication Data

US 2015/0083747 A1    Mar. 26, 2015

Related U.S. Application Data

(63) Continuation of application No. 12/101,446, filed on Apr. 11, 2008, now Pat. No. 8,881,332, which is a
(Continued)

(51) Int. Cl.
*B65H 3/00* (2006.01)
*A46B 11/00* (2006.01)
(Continued)

(52) U.S. Cl.
CPC .......... *A46B 11/0003* (2013.01); *A46B 9/025* (2013.01); *A46B 11/0006* (2013.01);
(Continued)

(58) Field of Classification Search
CPC . A46B 11/0003; A46B 9/025; A46B 11/0006; A46B 11/0068; A46B 15/0002;
(Continued)

(56) References Cited

U.S. PATENT DOCUMENTS

| 1,411,681 | A | * | 4/1922 | Burlew | ..................... A61K 8/02 |
| | | | | | 15/104.94 |
| RE19,006 | E | * | 11/1933 | Graves | ............... A46B 11/0003 |
| | | | | | 132/309 |

(Continued)

FOREIGN PATENT DOCUMENTS

| WO | 0226078 A2 | 4/2002 |
| WO | 2004021914 A2 | 3/2004 |
| WO | WO 2005110149 A2 * | 11/2005 ............. A46B 9/005 |

OTHER PUBLICATIONS

Kalili, T. et al., "Fluoride Absorption by Enamel from Toothpaste in Lowered pH Environment," J. Dent. Res. 83, Abstract #4033, 2004, 1 page.
(Continued)

*Primary Examiner* — Rakesh Kumar
(74) *Attorney, Agent, or Firm* — Withrow & Terranova, P.L.L.C.; Vincent K. Gustafson

(57) ABSTRACT

A toothbrush includes a brush head having a capsule receiving zone sized to receive a dentrifice capsule. A plurality angled bristles may retain the capsule in such zone. Loading of such toothbrush with a capsule may be performed with a dispenser including a toothbrush manipulation element adapted to move a retention structure associated with the brush head, and dispensation element adapted to deliver the capsule into the receiving zone. Such dispenser may include a desiccant material disposed to receive moisture from a capsule storage container. A dispenser may further include a plurality of toothbrush insertion apertures each adapted to receive a portion of a different toothbrush, so as to enable multiple users each having different toothbrushes to use the same dispenser without requiring contact between multiple brushes and single capsule interface surface of the dispenser.

20 Claims, 11 Drawing Sheets

Related U.S. Application Data continuation-in-part of application No. 11/840,627, filed on Aug. 17, 2007, now abandoned.

(51) Int. Cl.
    *A46B 9/02*         (2006.01)
    *A46B 15/00*      (2006.01)
    *A46B 17/06*      (2006.01)
    *A61C 19/06*      (2006.01)

(52) U.S. Cl.
    CPC ...... *A46B 11/0068* (2013.01); *A46B 15/0002* (2013.01); *A46B 15/0008* (2013.01); *A46B 15/0036* (2013.01); *A46B 17/06* (2013.01); *A61C 19/063* (2013.01); *A46B 2200/1066* (2013.01)

(58) Field of Classification Search
    CPC . A46B 15/0008; A46B 15/0036; A46B 17/06; A46B 2200/1066; A61C 19/063
    USPC .......................................... 221/289, 267, 264
    See application file for complete search history.

(56) References Cited

U.S. PATENT DOCUMENTS

| | | | |
|---|---|---|---|
| 1,950,767 A * | 3/1934 | Abbott | A46B 11/001 132/308 |
| 1,995,374 A * | 3/1935 | Young | A46B 11/00 206/540 |
| 2,004,957 A | 6/1935 | Messner | |
| 2,262,982 A * | 11/1941 | Wolcott | A46B 9/04 15/167.1 |
| 2,683,554 A * | 7/1954 | Mulhauser, Jr. | B65D 83/0409 221/152 |
| 2,778,045 A | 1/1957 | Bly et al. | |
| 3,191,803 A * | 6/1965 | Hamilton | A47K 5/18 141/360 |
| 3,471,056 A * | 10/1969 | Kovac | B65D 83/0418 221/151 |
| 3,962,417 A | 6/1976 | Howell | |
| 3,991,776 A | 11/1976 | Duffy | |
| 4,253,212 A | 3/1981 | Fujita | |
| 4,427,116 A | 1/1984 | Brown | |
| 4,753,792 A | 6/1988 | Aberg | |
| 5,178,878 A | 1/1993 | Wehling et al. | |
| 5,195,659 A | 3/1993 | Eiskant | |
| 5,230,440 A * | 7/1993 | Kurokawa | B65D 83/0418 221/198 |
| 5,616,299 A * | 4/1997 | Walker | B01L 99/00 221/197 |
| 5,864,288 A | 1/1999 | Hogan | |
| 5,894,926 A | 4/1999 | Stafford | |
| 5,960,801 A | 10/1999 | Vermooten et al. | |
| 6,027,273 A | 2/2000 | Li | |
| 6,106,294 A | 8/2000 | Daniel | |
| 6,131,765 A * | 10/2000 | Barry | A47F 1/035 221/264 |
| 6,154,912 A | 12/2000 | Li | |
| 6,524,023 B2 | 2/2003 | Andersen | |
| 6,845,883 B2 | 1/2005 | Pieri | |
| 6,988,638 B2 | 1/2006 | Zak | |
| 7,074,390 B2 | 7/2006 | MacKinnon | |
| 7,182,542 B2 | 2/2007 | Hohlbein | |
| 7,273,327 B2 | 9/2007 | Hohlbein et al. | |
| 7,575,387 B2 | 8/2009 | Atkin | |
| 7,651,012 B2 * | 1/2010 | Colman | A47K 5/18 222/105 |
| 7,748,565 B2 * | 7/2010 | Anvieh | A47K 1/09 141/361 |
| 8,113,729 B2 * | 2/2012 | Solan | A46B 11/0065 401/132 |
| 8,357,114 B2 * | 1/2013 | Poutiatine | A61J 7/0038 604/59 |
| 8,579,163 B2 * | 11/2013 | Ellis | A47K 5/18 206/369 |
| 8,881,332 B2 * | 11/2014 | Noble | A46B 9/025 15/167.1 |
| 9,332,827 B2 * | 5/2016 | Lee | A46B 9/04 |
| 2004/0091431 A1 * | 5/2004 | Alexander | A46B 11/00 424/49 |
| 2004/0094564 A1 * | 5/2004 | Papp | A61J 7/0084 221/25 |
| 2004/0185011 A1 * | 9/2004 | Alexander | A45D 40/24 424/49 |
| 2005/0069372 A1 | 3/2005 | Hohlbein et al. | |
| 2005/0260141 A1 | 11/2005 | Alexander | |
| 2006/0057078 A1 | 3/2006 | Rau | |
| 2006/0115435 A1 | 6/2006 | Wilkens | |
| 2006/0165473 A1 * | 7/2006 | Hohlbein | A46B 5/0062 401/132 |
| 2006/0245814 A1 * | 11/2006 | Papa | A47K 5/18 401/123 |
| 2006/0249419 A1 * | 11/2006 | Taylor | A61M 15/0045 206/528 |
| 2007/0075100 A1 * | 4/2007 | Colman | A47K 5/18 222/372 |
| 2007/0254260 A1 | 11/2007 | Alden, IV et al. | |
| 2008/0008728 A1 | 1/2008 | Atkin | |
| 2008/0014010 A1 | 1/2008 | Bartschi et al. | |
| 2008/0120798 A1 | 5/2008 | Sorrentino et al. | |
| 2009/0044356 A1 | 2/2009 | Noble et al. | |
| 2012/0054974 A1 * | 3/2012 | Hurwitz | A46B 9/04 15/167.1 |
| 2015/0083747 A1 * | 3/2015 | Noble | A46B 9/025 221/279 |

OTHER PUBLICATIONS

Non-Final Office Action for U.S. Appl. No. 12/101,446 dated Jul. 5, 2012, 6 pages.
Final Office Action for U.S. Appl. No. 12/101,446 dated Feb. 15, 2013, 8 pages.
Advisory Action for U.S. Appl. No. 12/101,446 dated May 16, 2013, 3 pages.
Non-Final Office Action for U.S. Appl. No. 12/101,446 dated Aug. 1, 2013, 7 pages.
Applicant-Initiated Interview Summary for U.S. Appl. No. 12/101,446 dated Sep. 23, 2013, 3 pages.
Final Office Action for U.S. Appl. No. 12/101,446 dated Dec. 19, 2013, 12 pages.
Advisory Action for U.S. Appl. No. 12/101,446 dated Apr. 18, 2014, 3 pages.
Notice of Allowance for U.S. Appl. No. 12/101,446 dated Sep. 17, 2014, 9 pages.

* cited by examiner

TOOTHBRUSH SYSTEM UTILIZING ORAL CARE CAPSULE

STATEMENT OF RELATED APPLICATIONS

This application is a continuation of U.S. patent application Ser. No. 12/101,446 filed on Apr. 11, 2008 and issuing as U.S. Pat. No. 8,881,332 on Nov. 11, 2014, which is a continuation-in-part of U.S. patent application Ser. No. 11/840,627 filed on Aug. 17, 2007, now abandoned. Benefit of the filing dates of such prior applications is claimed under 35 U.S.C. §120, and the disclosures of such prior applications are hereby incorporated by reference herein.

FIELD OF THE INVENTION

The present invention relates to oral care, and more specifically, to toothbrushes and dispensing systems utilizing oral care capsules.

DESCRIPTION OF THE RELATED ART

Good oral hygiene requires regular and proper attention to tooth brushing and flossing. According to the American Academy of Periodontology, chronic gingivitis (causing gum tissue to swell, turn red, and bleed easily) is common in children, but can be prevented and treated with a regular routine of brushing, flossing, and professional dental care. Absent treatment, chronic gingivitis can lead to more serious forms of periodontal disease.

Proper oral care habits can be difficult to instill in young children. Common challenges for caregivers of children include motivating children to initiate oral hygiene tasks, and to execute such tasks properly without assistance.

Even if motivation barriers are overcome, children often have difficulty in using conventional oral hygiene products and performing conventional oral hygiene methods. For example, many young children have difficulty in manipulating a toothbrush and toothpaste tube in separate hands and dispensing a proper amount from such a tube to the toothbrush. Avoiding generation of messes due to transfer of toothpaste to skin, clothing, and other surfaces during or after such dispensation may also be difficult for young children at a stage of physiological development where muscle control and general coordination are limited. Thereafter, children desiring to engage in other activities may be inclined to rush the task of brushing teeth without devoting the recommended time of two minutes or more to the task.

Conventional toothpaste dispensing systems further provide opportunities for not only growth of pathogens such as bacteria and virus, but also transfer of such pathogens from one toothbrush (or user) to another.

Oral care capsules, which avoid some of the mess associated with conventional toothpaste, are known. Examples of various oral care capsules are disclosed in U.S. Patent Application Publication No. 2005/0260141 to Alexander (hereinafter "Alexander"), U.S. Pat. No. 7,074,390 to MacKinnon (hereinafter "MacKinnon"), and U.S. Pat. No. 4,427,116 to Brown (hereinafter "Brown"), each of which is hereby incorporated by reference. Alexander discloses formation of variously shaped discrete toothpaste beads each having a dry exterior formed by locally applied processes such as heating, drying, extrusion, dusting, molding, varnishing, and coating. One or more beads are selected for use, removed from the container or dispenser, and broken open either by finger pressure, by pressing the bead against a brush or the user's teeth, or it may be bitten; after the internally stored as toothpaste is released into the mouth, a conventional toothbrush is used in the normal manner. (Alexander, ¶0081.) MacKinnon discloses formation of a dentrifice or toothpaste capsule, (optionally including miswak fibers) having a shell of choline, albumin, or gelatin. In use, a capsule according to MacKinnon is put into the user's mouth, the coating is broken with the teeth, and the toothpaste released thereby is distributed throughout the mouth using the tongue or a toothbrush. (MacKinnon, col. 2.) Brown discloses a capsule including a predetermined amount of toothpaste that is encapsulated with a covering (e.g., gelatin) that is preferably water-soluble and breakable when bitten or chewed. (Brown, col. 2). Thus, each of the preceding references require manual manipulation of an oral care capsule by the user.

Furthermore, each of the preceding references rely upon insertion of a capsule into the user's mouth, and such capsules may not be desirable or appropriate for use by small children. A very young user may liken a dentrifice capsule to candy, and be inclined to swallow it rather than use it in combination with a brush. If a capsule is very small in size, then multiple capsules may be required to deliver an appropriate amount of toothpaste to the user, and opportunities may abound for inconsistent application or waste. Alternatively, if a large capsule is too large in size, then it may pose a choking hazard for a young user.

Moreover, ensuring that the shell or coating of an oral care capsule is easily dissolved in the mouth of a user may limit the ability to practically store multiple capsules in a typical high-moisture bathroom environment. That is, if capsules are stored in a tightly sealed container to prevent moisture infiltration that may degrade a dissolvable coating, such container may be unsuitable for use by a small child. Alternatively, if capsules are stored in a less well-sealed container suitable for manipulation by a small child, moisture infiltration may degrade water-dissolvable capsule coating materials that may lead to spoilage of stored capsules.

Different users having dedicated toothbrushes may store and use such toothbrushes in a single bathroom. Contact between toothbrushes for different users should be minimized to prevent spread of pathogens from one user to another. If an oral care capsule is subject to use with a toothbrush, it would be desirable to avoid contact between toothbrushes for different users and an interface for an oral care capsule.

Thus, it would be desirable to provide toothbrushes and dentrifice dispensing systems that motivate children to initiate and perform oral care tasks properly, while minimizing dangers to such users, minimizing mess creation, reducing opportunities for pathogen growth, promoting consistent dentrifice dispensing, and promoting reliable dentrifice storage.

SUMMARY OF THE INVENTION

The present invention relates to toothbrushes and oral care (dentrifice) capsules, and methods of dispensing and using same, that are suitable for use by small children, and that overcome various limitations associated with such capsules.

In one aspect, the invention relates to a toothbrush comprising a brush head having a capsule receiving zone sized to receive an oral care capsule, and having a plurality of angled bristles adapted to retain an oral care capsule in the capsule receiving zone.

In another aspect, the invention relates to a dispensing device adapted for use with a toothbrush including a brush head (i) having a capsule receiving zone sized to receive an oral care capsule, and (ii) having a plurality of angled bristles adapted to retain an oral care capsule in the capsule receiving zone, the dispensing device comprising: a toothbrush manipulation element adapted to move a retention structure associated with the brush head to enable receipt of said oral care capsule; and a dispensation element adapted to deliver said oral care capsule into the capsule receiving zone.

In a further aspect, the invention relates to an oral care capsule dispensing device, comprising: a container having an interior adapted to contain a plurality of oral care capsules; a desiccant material disposed to receive moisture from the interior; and a selectively closable dispensing orifice adapted to permit dispensation of at least one oral care capsule from the container.

In a further aspect, any of the foregoing aspects may be combined for additional advantage.

Other aspects, features, and embodiments of the invention will be more fully apparent from the ensuing disclosure and appended claims.

DETAILED DESCRIPTION OF THE INVENTION, AND PREFERRED EMBODIMENTS THEREOF

Figure 1:
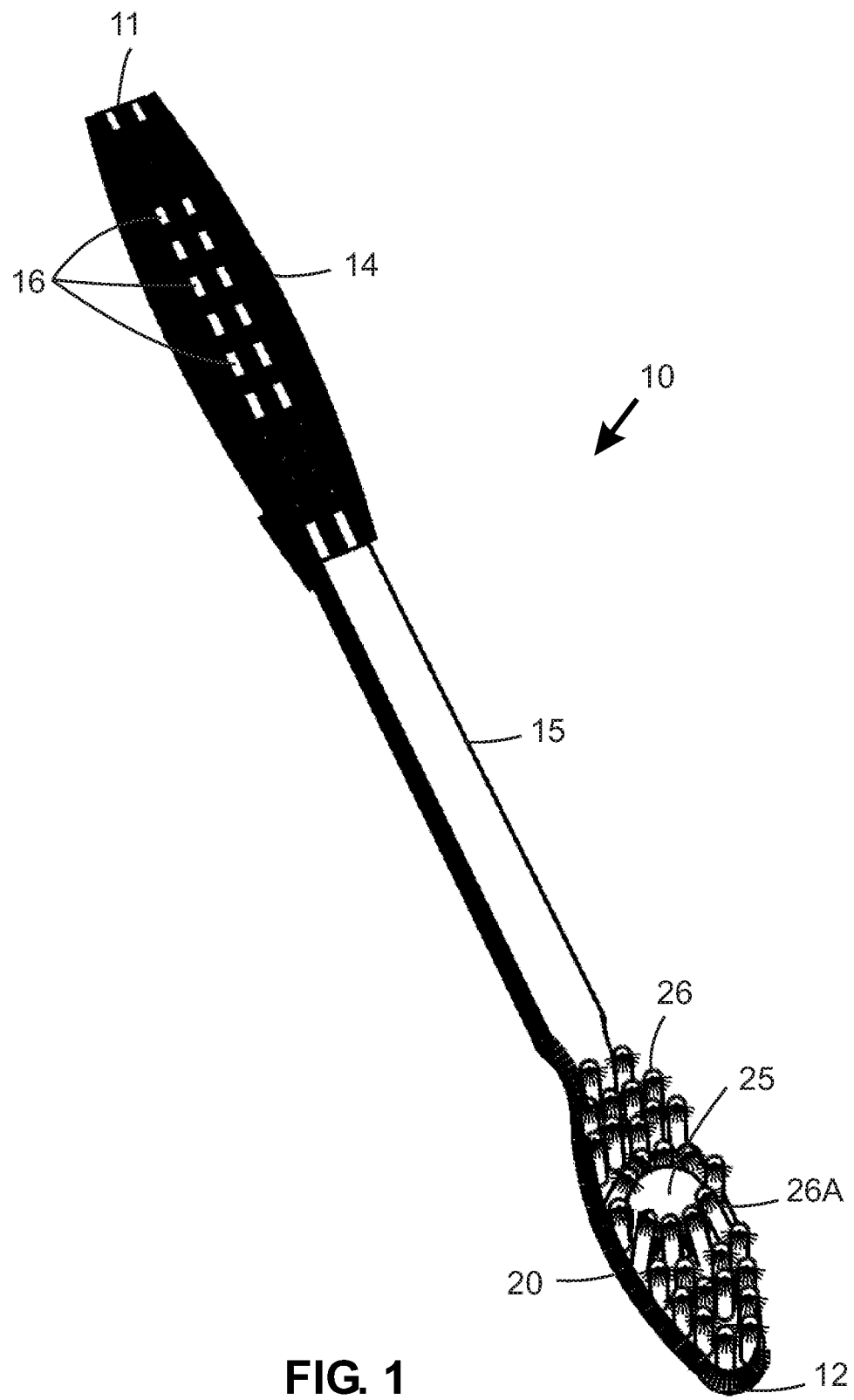
FIG. 1 is a perspective upper view of a toothbrush according to one embodiment of the present invention, the toothbrush having angled bristles adapted to receive and retain an oral care capsule for use in cleansing teeth and gums of a user.

The present invention relates to a toothbrush adapted to receive and retain an oral care capsule, and to a dispensing device adapted to supply at least one oral care capsule to such a toothbrush.

As indicated previously, various types of oral care or dentifrice capsules, and methods of making same, are known. At least an exterior portion of each capsule includes a solid material, such as gelatin, that is dissolvable in water and/or saliva (e.g., in the mouth of a user). Use of such dentifrice capsules provides multiple advantages over conventional flowable toothpastes subject to dispensation by displacement from a flexible tube. A measured and reproducible quantity of dentifrice is included in each capsule. Potential for transfer of paste material to undesired surface following dispensation but prior to use is substantially eliminated. A capsule or portion thereof may include a dissolution time profile that may be used as a guide for desirable brushing duration.

A preferred capsule is spherical or spheroidal (approximately spherical) in shape, to provide volumetric efficiency and substantially uniform dissolution of at least an exterior portion thereof. The composition of a capsule can be varied with respect to radius, to provide any one or more of various functions. For example, an outer or near-outer layer may comprise an effervescent layer with micro-abrasives to assist in cleaning the teeth and gums. Various effervescent materials and related additives suitable for oral use and/or ingestion, and methods for making same, are disclosed in U.S. Pat. No. 5,178,878, U.S. Pat. No. 4,753,792, and U.S. Pat. No. 3,962,417, which are hereby incorporated by reference. A plaque colorant layer may be provided to render plaque formed on teeth immediately visible to the naked eye of the user. A pH lowering layer may be provided to lower the pH environment in the user's mouth, as has been recently determined to promote absorption of fluoride into the user's teeth due to the lowered pH environment. (See, e.g., T. Kalili, et al., "Fluoride Absorption by Enamel from Toothpaste in Lowered pH Environment," J. Dent. Res. 83 (Spec Iss A) Abstract #4033 (2004).) Such pH lowering layer may be time-released to maintain pH at a target value for a desired period of time. One or more neutralizing and/or decolorant agents may be provided to neutralize pH and/or attenuate or remote the plaque colorant material, such as to avoid lasting effect of the plaque colorant. An oral care tablet with a plaque color indicator and decolorizing agent is disclosed in U.S. Patent Application Publication No. 2006/0115435, which is hereby incorporated by reference. One or more flavoring layers may be provided. A dentifrice layer (e.g., in solid, gel, or paste form), including abrasive materials such as silica may be further provided within the capsule. Further possible layers include a whitening layer (e.g., containing a peroxide), an anticalculus (anti-tartar) layer, a whitening layer (e.g. including a peroxide material), an antibacterial layer (e.g., including triclosan), and a breath freshening layer. Any two or more of the foregoing layers may overlap or be combined as desirable for simultaneous effect, or may be separated (e.g., by an intermediate gel layer) as desirable or necessary, and any combination of the foregoing layers may be provided in a single capsule. In terms of external appearance, capsules may be provided in various colors or patters, and may further be printed with words or pictures such as corresponding to media characters.

Figure 2:
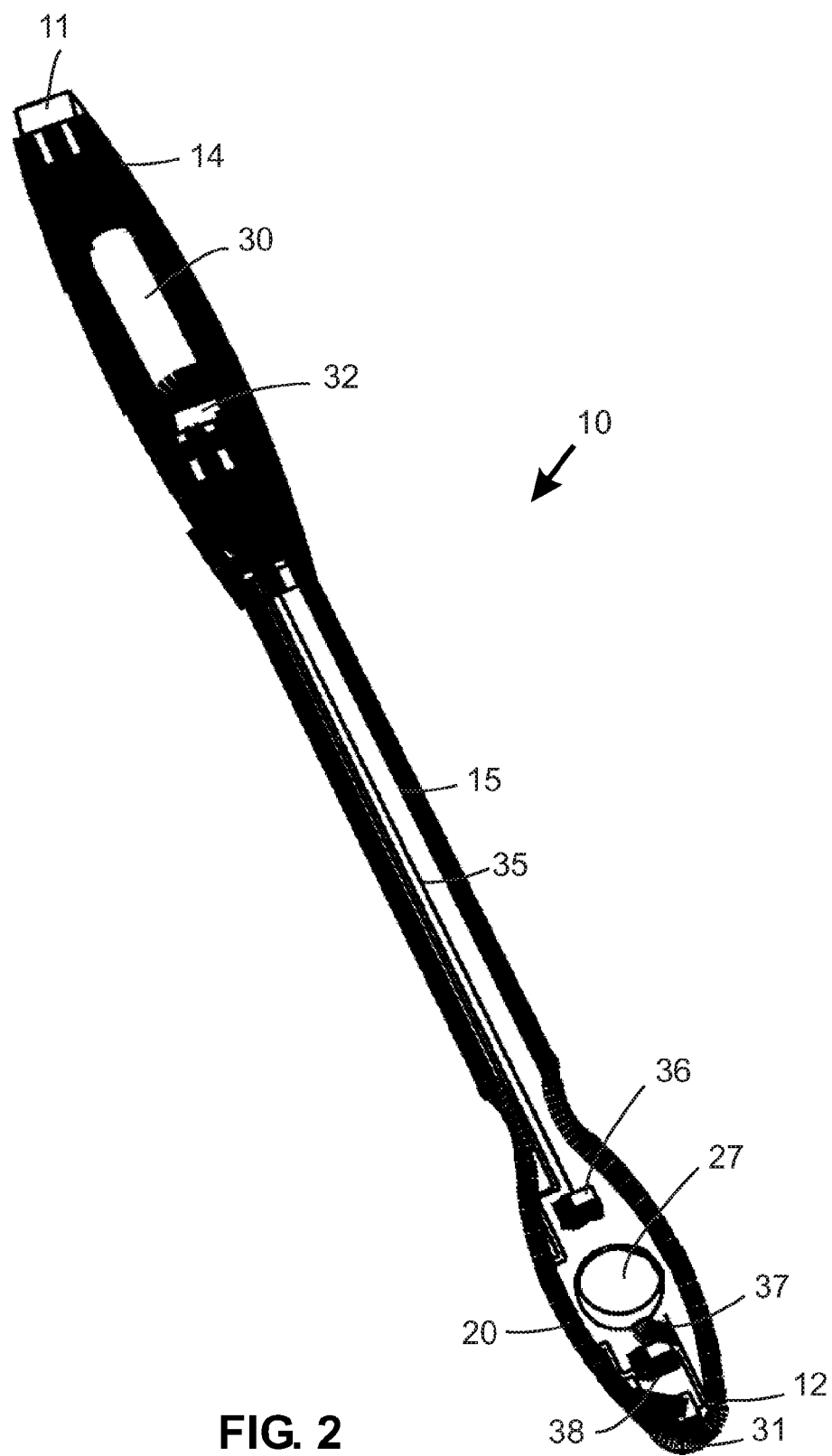
FIG. 2 is a perspective upper view of an internal portion of the toothbrush of FIG. 1 according to one embodiment of the present invention.
Figure 4:
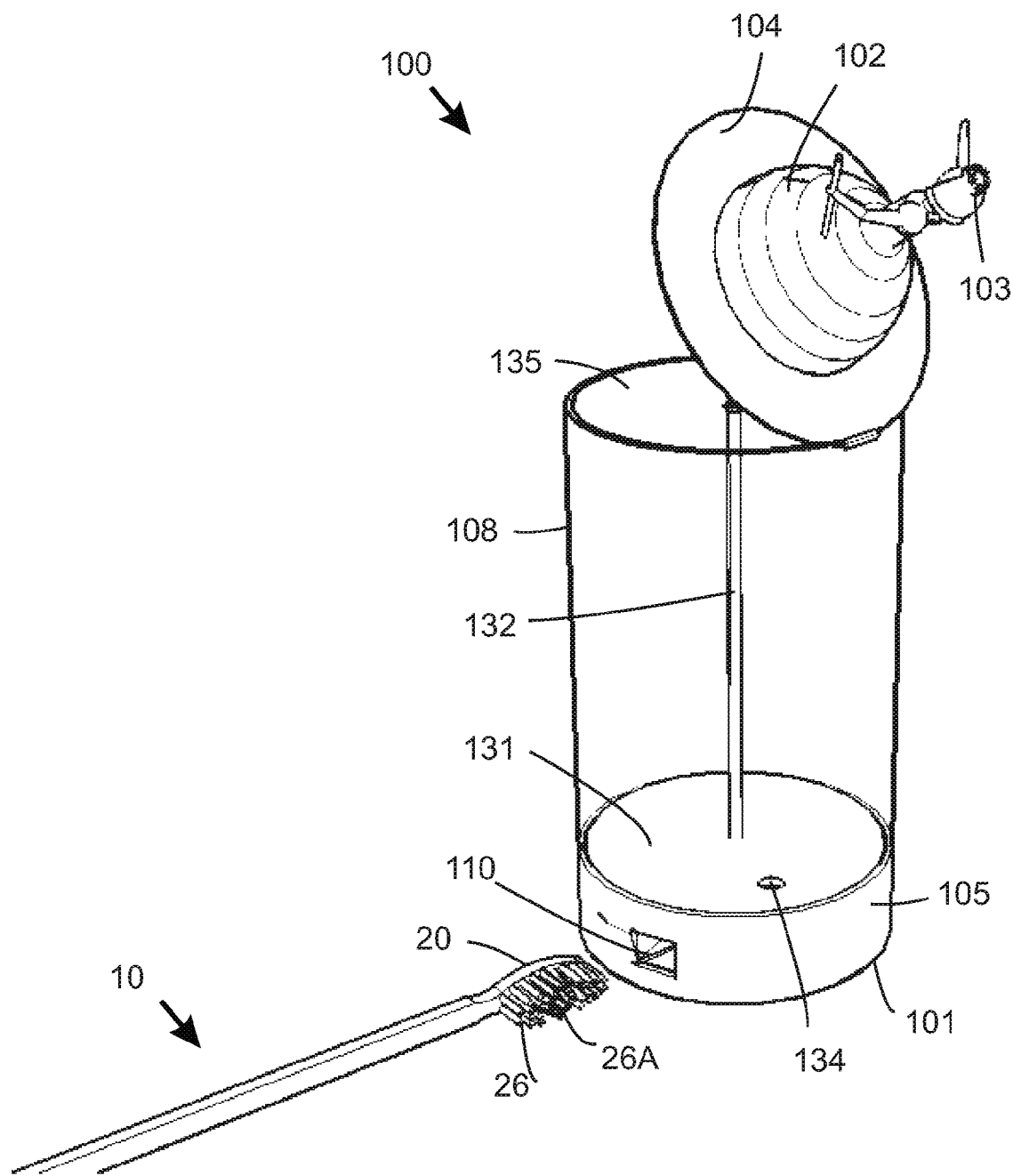
FIG. 4 is a perspective view of the toothbrush of FIGS. 1-2 positioned for insertion into a side aperture of the dispenser of FIG. 3 to permit the toothbrush to receive an oral care capsule.
Figure 5:
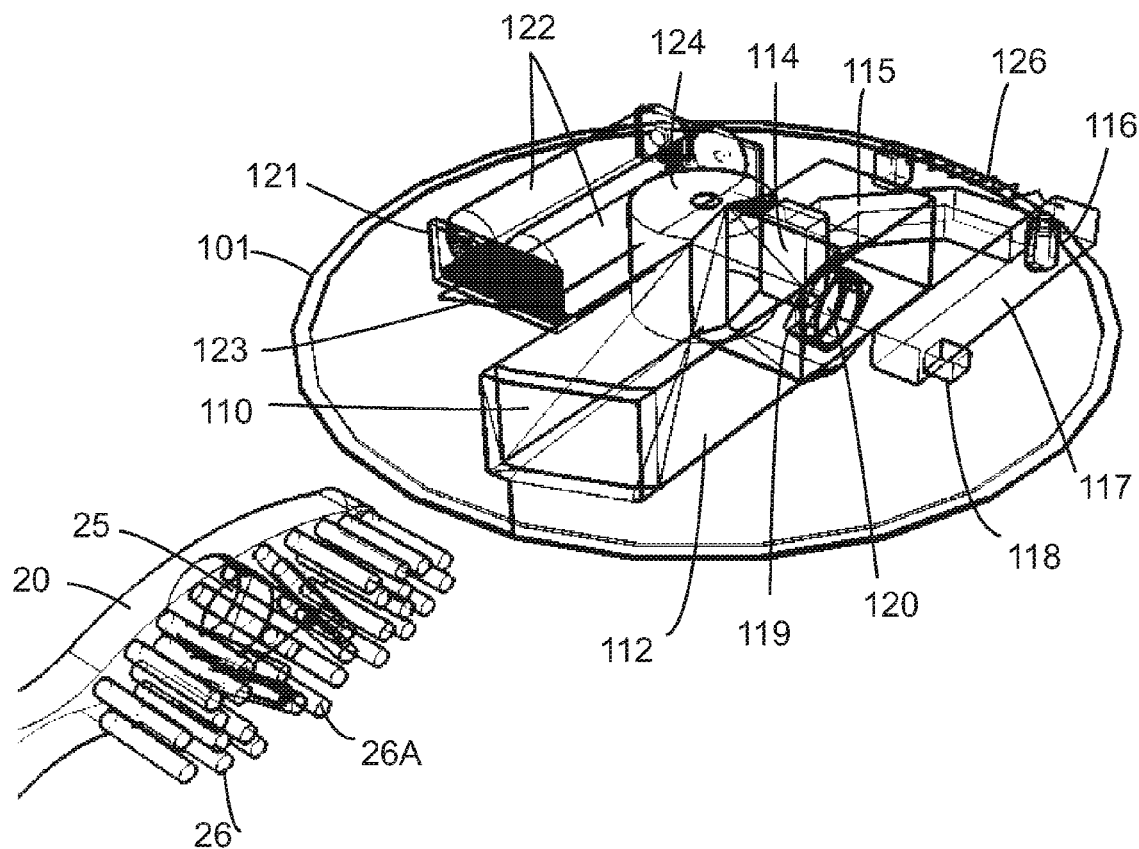
FIG. 5 is a side perspective view of a first internal loading portion of the dispenser of FIGS. 3-4 having an integral bristle spreader, and a portion of the toothbrush of FIGS. 1, 2, and 4 positioned for insertion into a side aperture of the dispenser portion.

A toothbrush 10 adapted to receive and retain an oral care capsule is illustrated in FIGS. 1-2. The toothbrush 10 includes a handle 14 disposed along a first end 11 optionally including a dial or switch 33, an intermediate shaft 15, and a brush head 20 disposed along a second end 12 optionally having an activation element 31. The brush head 20 includes a capsule receiving zone 25, such as may include a recess defined in the brush head 20, disposed within a plurality of angled bristles 26A. The angled bristles 26A are preferably canted away from vertical in a direction toward the center of the capsule receiving zone 25, so as to retain an oral care capsule (not shown) insertable into the capsule receiving zone 25. The size and shape of the capsule receiving zone 25, and the size, spacing, and angle of the angled bristles 26A, are selected to retain an oral care capsule of a predetermined size and shape. As shown in FIGS. 1, 4, and 5, ten angled bristles 26A are equally spaced around the perimeter of a circular recess (spanning 360 degrees) defining the capsule receiving zone 25. Conventional straight bristles 26 may be further provided apart from the capsule receiving zone 25.

In the present embodiment, an oral care capsule is loaded into the toothbrush 10 by spreading the angled bristles 26A apart, and then inserting the capsule past the spread bristles into the oral care capsule receiving zone 25. In another embodiment to be described in more detail hereinafter, a toothbrush may include a moveable retaining element bounding a capsule receiving zone (e.g., from behind) and permitting an oral care capsule to be loaded without spreading apart bristles of the toothbrush.

One or more signalling elements 16 adapted to provide a user-perceptible signal may be disposed in or along the toothbrush handle 14. Such signal may be any of visible, auditory, and vibratory in nature. The one or more signaling elements 16 may provide a signal indicative of any of oral care cleansing cycle time and attainment of a threshold oral care cleansing cycle time, to ensure that the user engages in an oral cleansing operation of an optimally effective duration (e.g., two minutes or more). A threshold oral care cleansing time may be set or adjusted by the user with an input element, such as the dial or switch 33 or a separate interface element adapted to communicate with the toothbrush 10 for programming.

The handle 14 preferably includes a battery 30 or other charge storage element. The brush head 20 may include various signalling elements 36, 37, such as LEDs, sound generators, and/or vibration generators. One or more sensors 38 may be further provided to sense one or more conditions indicative of usage of said toothbrush 10 in an oral care cleansing cycle. For example, the one or more sensors 38 may sense any of motion, acceleration, vibration, and pressure. Signals generated by the one or more sensors 38 may be used, for example, in conjunction with a timer to determine time elapsed in an oral care cleaning cycle, or whether a minimum threshold oral care cleansing cycle has been satisfied. Alternatively, the activation element 31 may be depressed or otherwise activated at the beginning of an oral care cleansing cycle, and used to initiate a time for determining time elapsed in an oral care cleansing cycle or whether a minimum threshold time has been satisfied.

Circuitry 32 adapted to perform any of various desirable functions disclosed herein may be disposed in the handle 14. For example, the circuitry 32 may control signalling elements 16, 36, 37 provide timer functionality, store or allow adjustment of a threshold oral care cleansing cycle time, and the like. One or more conductors 35 may be disposed between the handle 14 and the brush head 20 to permit electrical communication between the battery 30 and/or circuitry 32 disposed in the handle 14, and the various electrically operable elements (e.g., signalling elements 36, 37, sensor 38, activation element 31) disposed in the brush head 20. In a preferred embodiment, the brush head 20 comprises a substantially optically transmissive material, such as to enable external transmission of light from one or more light emitting diodes or the like.

The capsule receiving zone 25 may include a recess formable by various means. In one embodiment, such a recess is defined by forming an aperture 27 through an intermediate portion of the brush head 14, and then closing the recess from behind with a cover (not shown). Alternatively, such a recess may be formed by conventional molding or other shaping techniques.

While a manually operated toothbrush 10 is shown, an electrically operated toothbrush with the same features as described herein is specifically contemplated as encompassed by the present invention.

As indicated previously, a toothbrush may include a moveable retaining element bounding a capsule receiving zone and permitting an oral care capsule to be loaded without spreading apart bristles of the toothbrush. For example, a rear portion of a brush head may include a hinged or slidable portion (e.g., a cover) that may be moved to an open position to expose an oral care capsule loading aperture. Such cover may be moved through operation of a corresponding toothbrush manipulation element associated with an oral care capsule dispensing device. Upon movement of such moveable retaining element to an open position, the oral care capsule is loaded into the oral care capsule loading aperture that constitutes an oral care capsule receiving zone. Thereafter, the moveable retaining element is returned to a closed position, and the oral care capsule is retained from behind by the retaining element, and preferably also from above by a plurality of angled bristles. In this regard, the moveable cover functions to selectively cover or obstruct the oral care capsule loading aperture.

In another embodiment, a brush head of a toothbrush includes a flexural portion adapted to permit at least some bristles of a plurality of angled bristles to be spread apart so as to enable an oral care capsule to be loaded in a capsule receiving zone of such brush head. An associated dispensing device may include a corresponding structure adapted to automatically effectuate such flexure of the brush head to permit loading of at least one capsule into a capsule receiving zone defined therein. Following a loading operation, flexing force is released from the brush head to cause the brush head to return to a relaxed position with an oral care capsule retained in the capsule receiving zone by the angled bristles.

Figure 3:
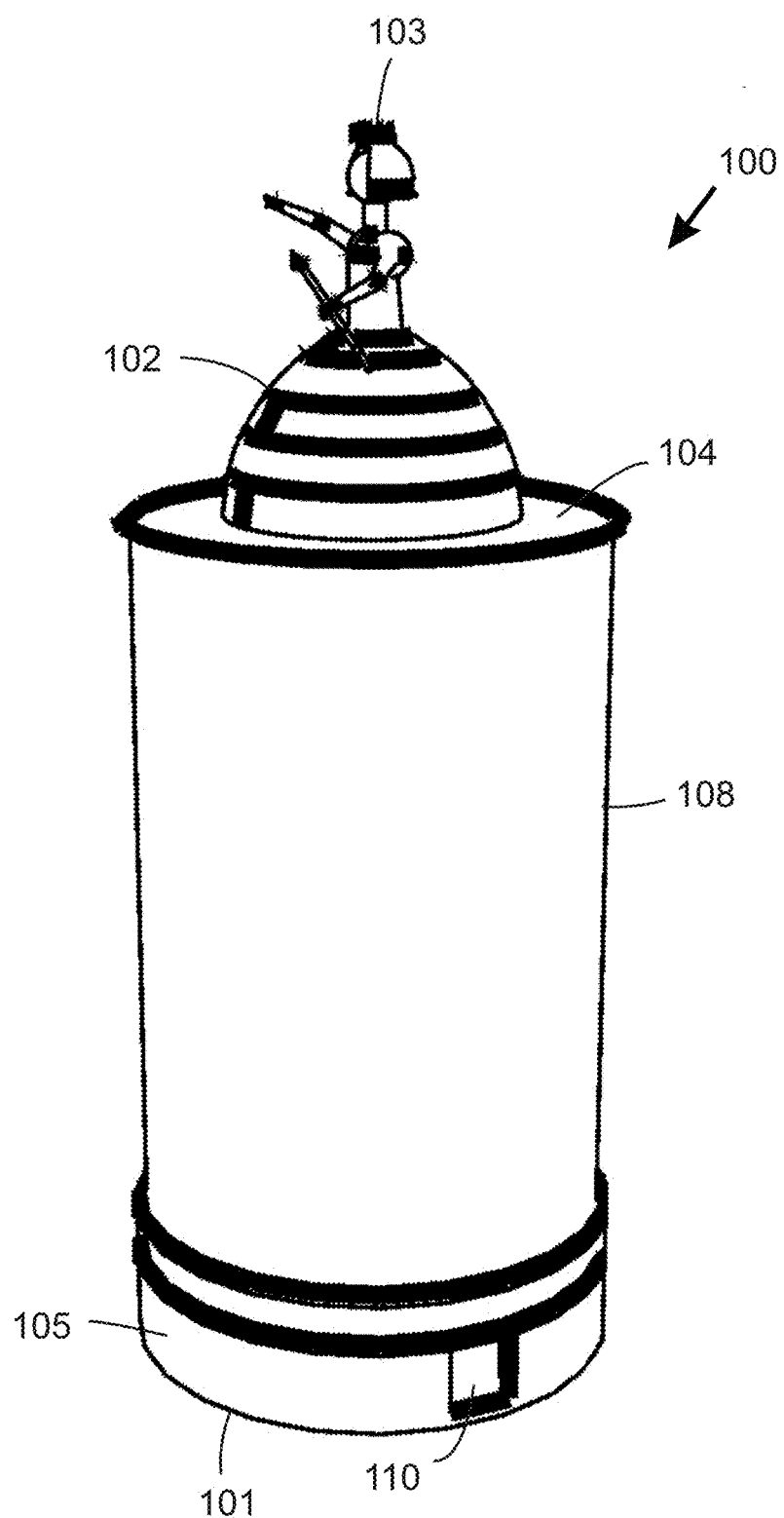
FIG. 3 is a perspective side view of the exterior of a dispenser for oral care capsules according to one embodiment of the present invention, the dispenser being adapted for use with the toothbrush of FIGS. 1-2.

A dispenser 100 for oral care capsules, adapted for use with the toothbrush 10, is illustrated in FIG. 3, with various portions thereof illustrated in the ensuing FIGS. 4-10.

Figure 8:
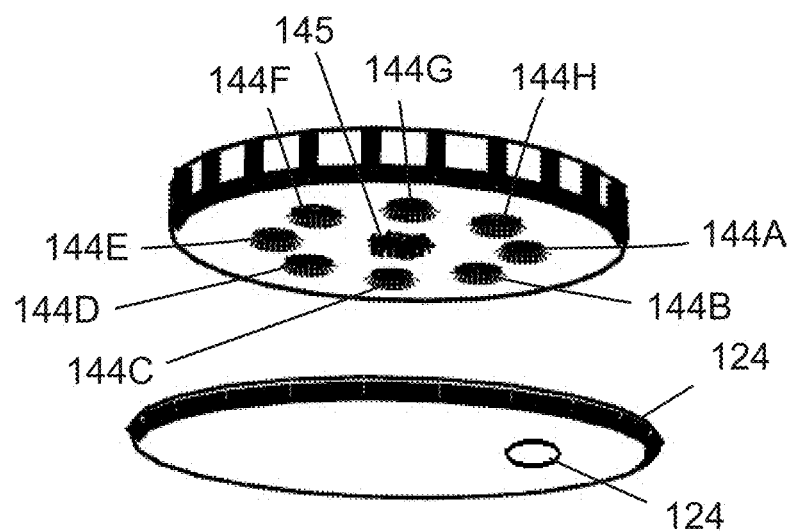
FIG. 8 is a side perspective assembly view of a second dispensing portion of the dispenser of FIG. 3 and the first loading portion of FIG. 5, with the second dispensing portion including a rotatable distribution plate having multiple apertures adapted to receive oral care capsules, and a dispensation plate adapted to permit passage of a single capsule from the distribution plate to the first loading portion.
Figure 8:
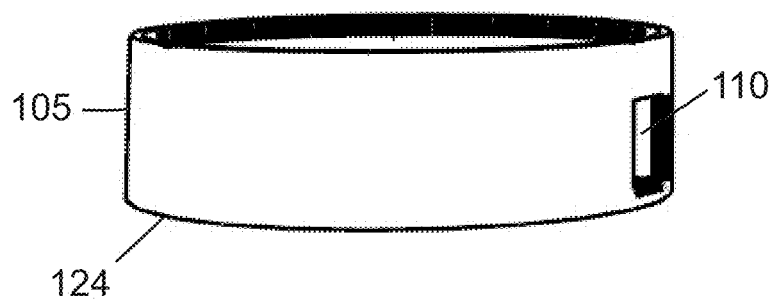
Figure 9:
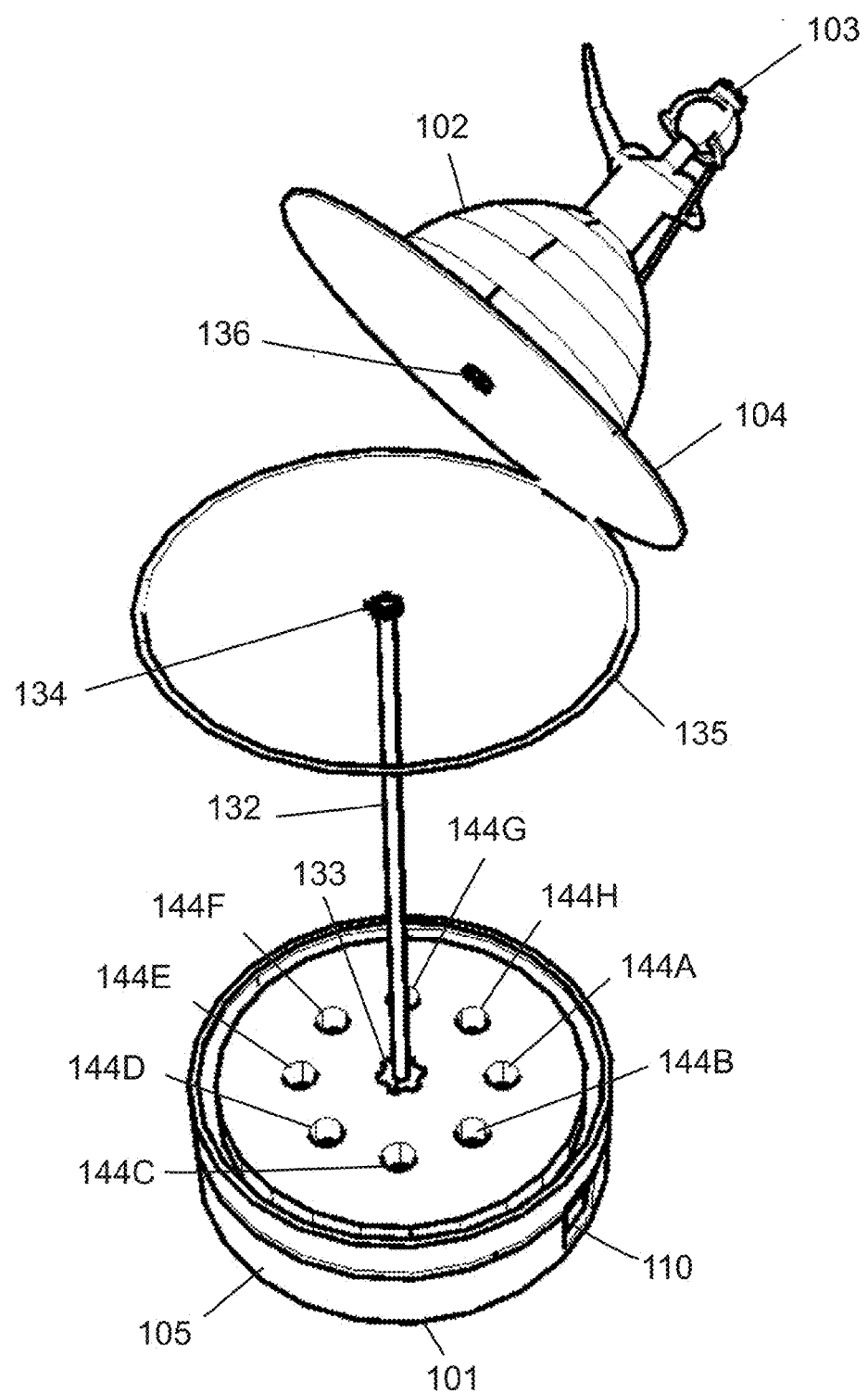
FIG. 9 is an upper perspective view of the assembled first and second dispenser portions of FIG. 8, coupled to a vertically protruding shaft affixed to a container cover having a hinged decorative lid.

The dispensing device 100 includes a bottom surface 101, a base portion 105, a container 108, and an outer lid 104. The container 108 may be formed of a translucent or substantially optically transmissive material to permit viewing of the contents therein. The container 108 may include a ramp (not shown), such as may be configured in a helical or spiral shape, to guide oral care capsules to a desired location (such as toward a distribution plate 141, as illustrated in FIGS. 8-9). The outer lid 104, which may be pivotally coupled to the container portion 108, optionally includes a figurine 102 and one or more light elements 103, such as may be provided in view of a user for entertainment utility. A toothbrush insertion aperture 110, sized and shaped to receive at least a portion of a toothbrush, is defined in the base portion 105.

Referring to FIG. 4, a toothbrush 10 may be oriented as shown for insertion into the toothbrush receiving aperture 110 of the dispensing device 100. The bottom surface 101 may be equipped with a non-skid material or a suction cup to prevent displacement of the dispensing device 100 upon insertion of a portion of a toothbrush 10 therein.

Disposed above the base portion 105 of the dispensing device 100 is a container 108 adapted to retain a plurality of oral care capsules (not shown) therein. A rotatable vertical shaft 132 may be provided along a vertical axis of the container 108 to mechanically couple the container 108, via inner lid 135 thereof, to a motor 124 (illustrated in FIG. 5). By way of such coupling, the outer lid 104 and figurine 102, along with distribution plate 141 (shown in FIGS. 8-9) may be caused to rotate through operation of the motor. If desired, the container 108 or a portion thereof may be coupled to rotate by operation of the motor 124 for user entertainment and/or dispensing utility. An orifice plate 131, defining an orifice 134 adapted to permit the passage of an oral care capsule in the base portion 105, is disposed below the container 108.

Figure 6:
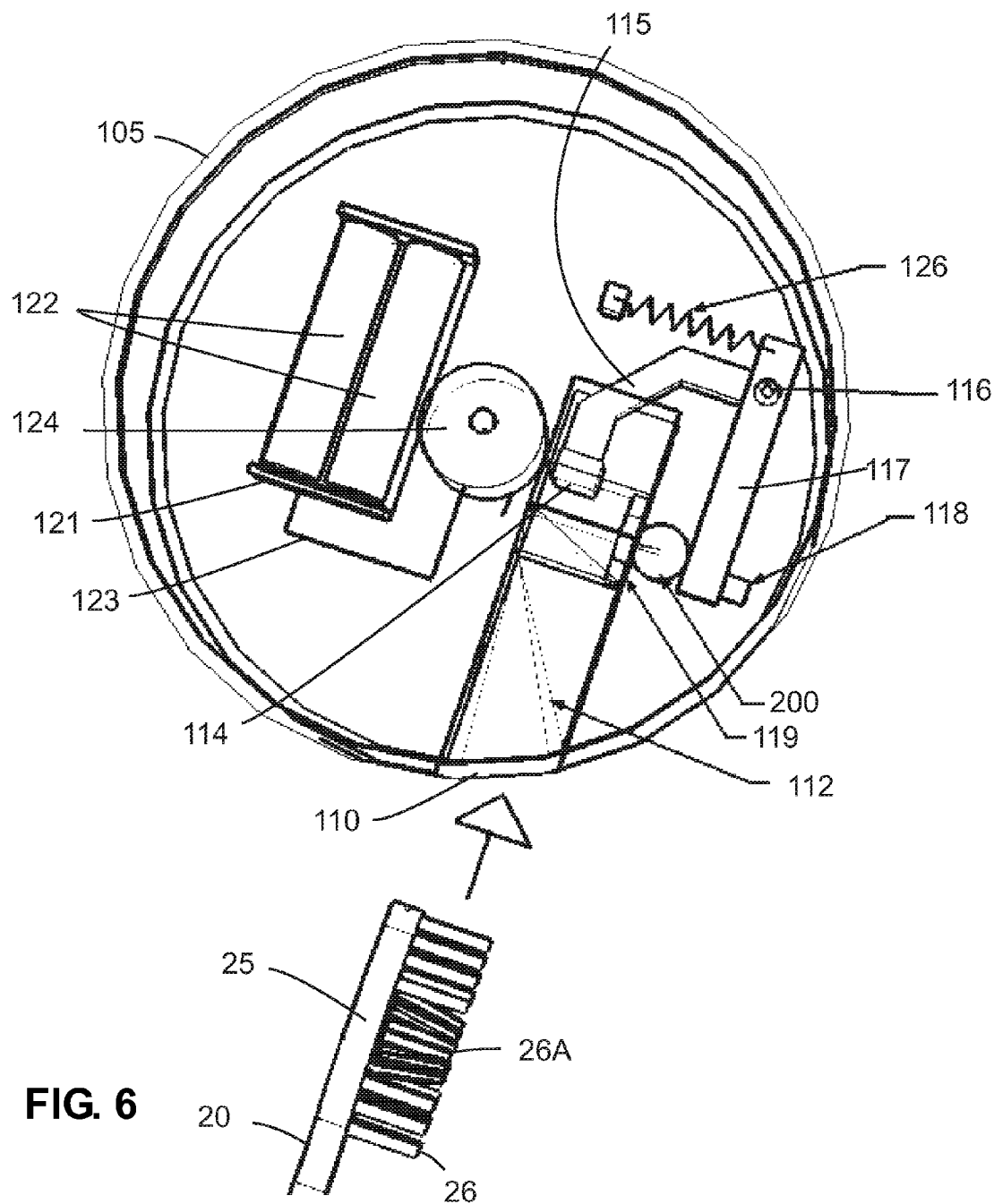
FIG. 6 is a top perspective view of the dispenser portion and the toothbrush portion of FIG. 5.
Figure 7:
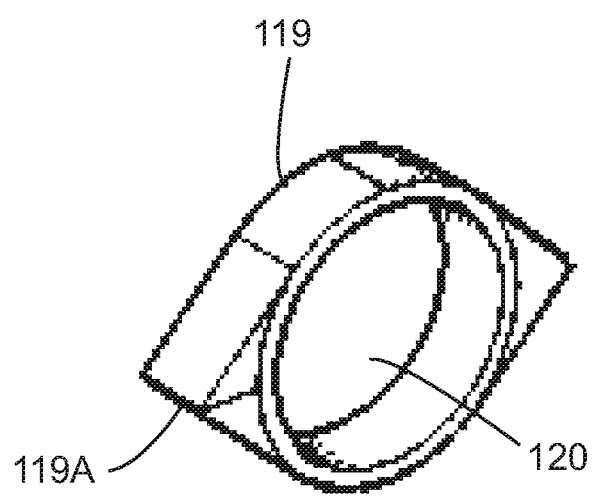
FIG. 7 is a perspective view of the bristle spreader of the dispenser portion of FIGS. 5-6.

FIGS. 5-6 illustrate selected internal components of the base portion 105 as positioned relative to a brush head 20 positioned for insertion therein. The toothbrush insertion aperture 110 leads to a guide tube 112 that guides the brush head 20 into position for loading of an oral care capsule therein. Disposed within the guide tube 112 is a toothbrush manipulation element in the form of a bristle spreader 119 defining an aperture 120 and having a wedge-shaped leading edge 119A. Such leading edge 119A may be configured as a wedge or block adapted to provide the desired spreading functionality. A close-up perspective view of the bristle spreader 119 is shown in FIG. 7. As the brush head 20 is inserted past the bristle spreader 119, the wedge-shaped leading edge 119A of the bristle spreader 119 spreads apart the angled bristles 26A to prepare the brush head 20 to receive an oral care capsule. Although the illustrated embodiment is directed to a specific mechanical oral care capsule loading mechanism, various other mechanically or electrically actuated means may be used, as will be recognized by those skilled in the art, to provide automatic dispensing operation. In the illustrated embodiment, the brush head 20 is inserted into the guide tube 112 to contact a push bar 114 joined via arm 115, a lever 117 having an associated pivot 116, and return spring 126. Upon depressing the push bar 114, the lever 117 is forced toward the guide tube 112 and the aperture-defining bristle spreader 119 disposed therein. In this manner, an oral care capsule 200 disposed between the lever 117 (e.g., opposite tab 118) may be pushed through the aperture 120 of the bristle spreader 119, past the spread-apart angled bristles 26A, and into the oral care capsule receiving zone 25 of the brush head 20 of the toothbrush 10. Upon removal of the brush head 20 from the bristle spreader 119, the angled bristles 26A return to their relaxed position to contract around an oral care capsule disposed within the capsule receiving zone 25.

Although FIG. 6 illustrates loading of an oral care capsule 200 laterally in a toothbrush head 20, a dispensing device may be configured for capsule loading in any desired direction. In one embodiment, a dispensing device is adapted to load an oral care capsule in an upward direction into a capsule receiving zone of a corresponding toothbrush head. In yet another embodiment, a dispensing device is adapted to load an oral care capsule in a downward direction into a capsule receiving zone of a corresponding toothbrush head.

FIGS. 5-6 further illustrate a battery holder 121 including two batteries 122 and a motor 124 coupled to receive power from the batteries 122 via cable 123. Such motor 124 may be used to set in motion any desired portion of the dispensing device 100, such as the container 108, figurine 102, and/or distribution plate 141 (illustrated in FIGS. 8-9). As an alternative to batteries 122, the dispensing device may be operated via alternating current input with an appropriate internal AC/DC converter (not shown).

The dispensing device 100 may further include a sterilization element, such as an ultraviolet light or other element (not shown), disposed in, along, or proximate to the guide tube 112. Such sterilization element may be activated upon insertion of a brush head 20 into the guide tube 112 to effect sterilization of the brush head 20 and therefore avoid pathogen growth (e.g., along any of the brush head 20, the guide tube 112, the spreading element 119, and the push bar 114) and potential for transfer of pathogens from one surface (or toothbrush) to the next. Such sterilization element may be operated by the batteries 122 or another power source. Moreover, any surfaces subject to contacting a toothbrush insertable into the dispensing device 100, and even the toothbrush 10, may be coated or otherwise formed with an antibacterial substance such as 5-chloro-2phenol (2,4dichlorophenoxy) commonly sold under the trade name Microban®.

Referring to FIGS. 8-9, the dispensing device 100 preferably includes a rotatable distribution plate 141 including a plurality of apertures 144A-144H each sized to receive an oral care capsule, with the distribution plate 141 disposed above the orifice plate 131. The apertures 144A-144H of the distribution plate 141 are positioned to permit oral care capsules disposed therein to drop into the orifice 134, preferably one at a time, upon rotation of the distribution plate 141. The orifice 134 of the orifice plate 131 is disposed immediately above the oral care capsule 200 shown in FIG. 6, such that an oral care capsule 200 that falls through the orifice 134 is ready for loading through the aperture 120 of the bristle spreading element 119 into a brush head 20 inserted into the guide tube 112. The distribution plate 141 further includes a central aperture 145 that is keyed or otherwise shaped to receive a lower torque transfer element 133 associated with the shaft 132, to rotate the distribution plate 141 without slippage. Likewise, the outer lid 104 may include an aperture 136 that is keyed or otherwise shaped to receive an upper torque transfer element 134 associated with the shaft 132, to permit the outer lid 104 and optional figurine 102 to rotate as well. Electrical contacts may be further provided through the shaft 132, torque transfer elements 133, 134, and aperture 136 to supply electrical power to the signalling element 116 (e.g., LED) associated with the figurine 102.

The distribution plate 141 is preferably closely spaced relative to the orifice plate 131, and one or more seals (not shown) may be provided therebetween. Any of the distribution plate 141 and orifice plate 131 may be formed or coated with a friction-reducing material, such as polytetrafluoroethylene (PTFE) to minimize wear or possible binding therebetween. Between dispensing cycles, the distribution plate 141 preferably rests in a position wherein none of the apertures 144A-144H are aligned with the orifice 131 of the orifice plate 134. This promotes sealing of the container 108, so as to minimize infiltration of moisture into the container 108 that might otherwise degrade water-dissolvable capsule shell or coating materials.

Figure 10:
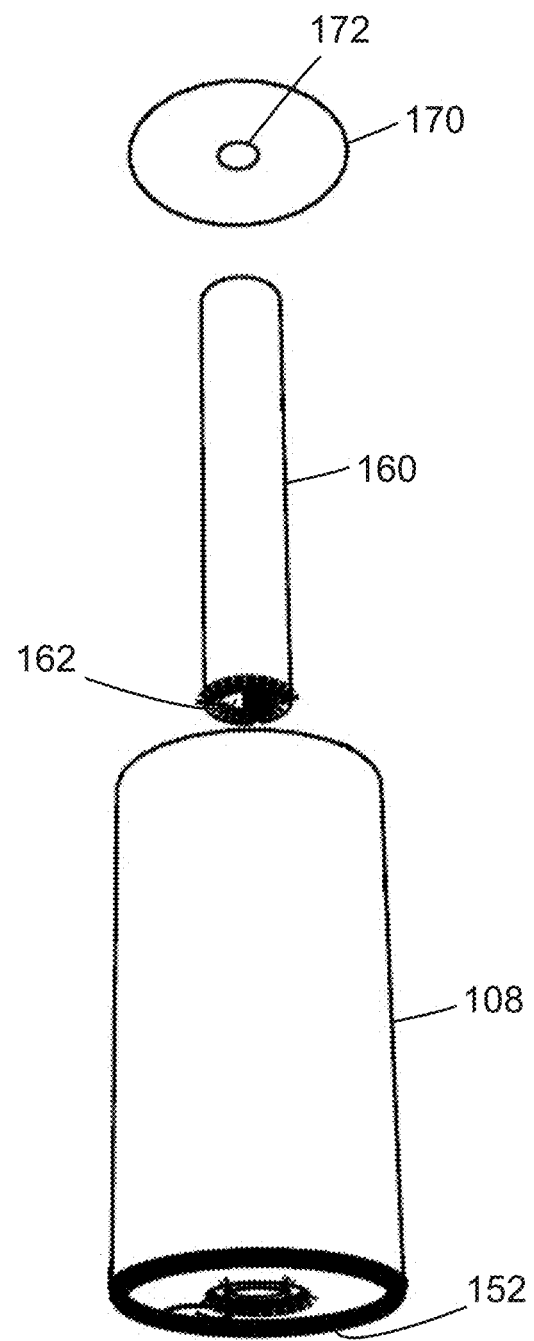
FIG. 10 is a side perspective assembly view of a third portion of the dispenser of FIG. 3, including a cylindrical container adapted to store multiple oral care capsules, and a desiccant element insertable into the container.

As toothbrushes are conventionally utilized in bathroom environments that may be quite moist, and oral care capsules may have water-dissolvable outer shell or coating materials, it is desirable to minimize presence of moisture in a container 108 having a plurality of oral care capsules disposed therein. Referring to FIG. 10, in one embodiment a desiccant material 160 may be disposed to receive moisture from the container 108. Such desiccant material 160 may be provided at a central portion of the container 108 or in any other desired location. Such desiccant material 160 may include a moisture absorbing board, silica gel, clay, or a molecular sieve, whether disposed loosely or packed, in a (e.g., mesh) pouch or other permeable retainer, disposed in moisture receiving relationship relative to the interior of the container 108. A cover 170 defining an aperture 172 may be provided over the desiccant 160 and the container 108. Such cover 170 may be permanently sealed to the container 108, or may be removable to permit replacement of the desiccant material 160.

The container 108 preferably comprises a cartridge that may be removed from the dispensing apparatus and replaced by the user. Such container may alternatively be refilled by the user through a capsule insertion port (not shown).

Figure 11:
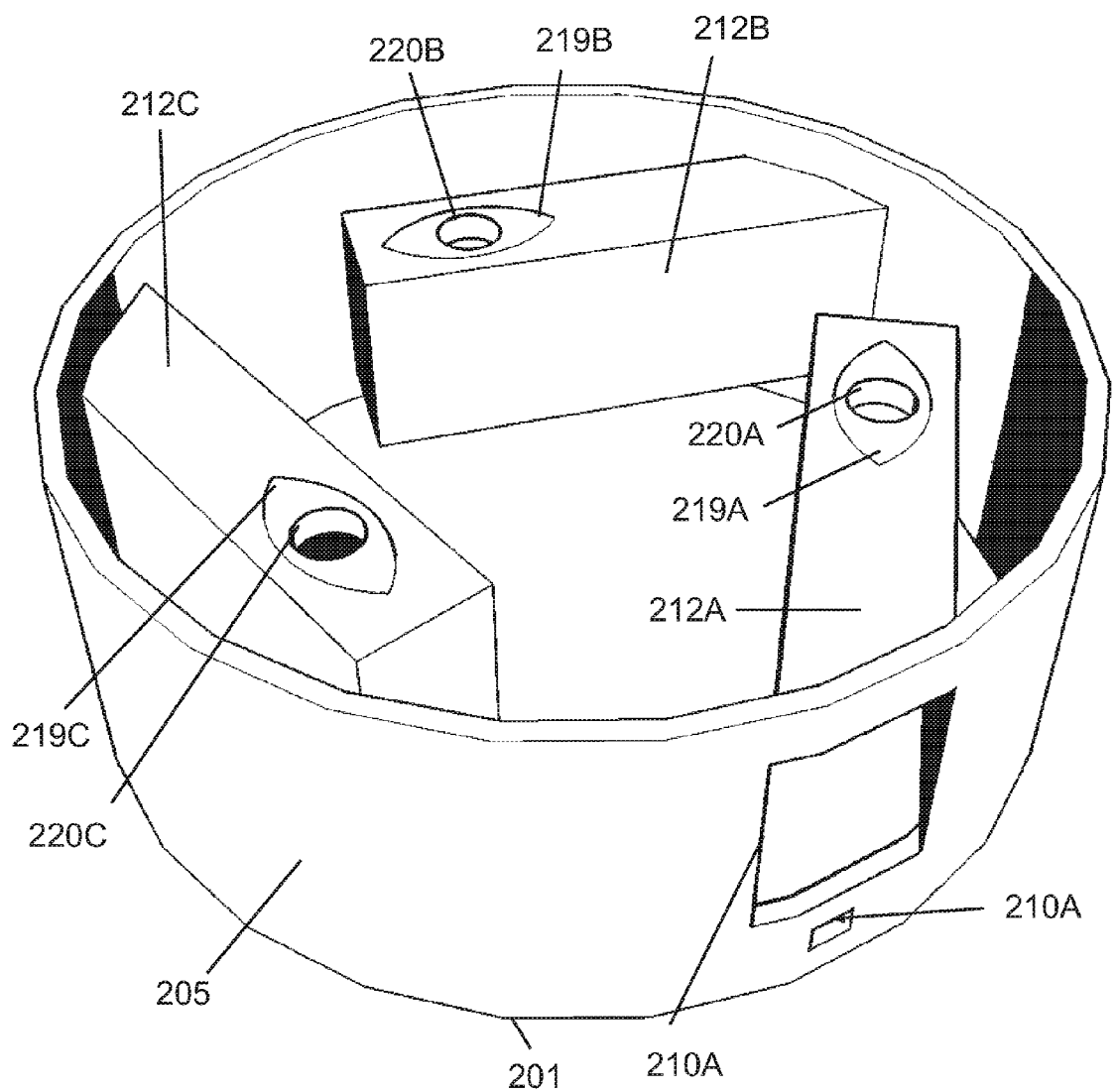
FIG. 11 is a perspective view of a base portion of an oral care capsule dispenser including multiple toothbrush insertion apertures and guide tubes, each adapted to receive a toothbrush of a different user.

In another embodiment, a dispensing device includes a plurality of toothbrush insertion apertures each adapted to receive a portion of a different toothbrush, so as to enable multiple users each having different toothbrushes to use the same dispenser without requiring contact between multiple brushes and single capsule interface surface of the dispenser. Such dispenser may resemble the dispensing device 100 described hereinabove with reference to FIGS. 3-4, but modified to include multiple toothbrush insertion apertures and guide tubes each intended to receive a different toothbrush. Referring to FIG. 11, a base portion 205 of a dispensing device has a bottom surface 201 and includes three guide tubes 212A-212C. Each guide tube 212A-212C has an associated toothbrush insertion aperture (e.g., toothbrush insertion aperture 210A for guide tube 212A is shown; it is to be understood that corresponding toothbrush insertion apertures are provided for guide tubes 212B, 212C) adapted to receive a portion of a different toothbrush. Each guide tube 212A-212C has an associated bristle spreading element 219A-219C adapted to spread apart bristles of a toothbrush as described hereinabove, to permit an oral care capsule to be supplied to the toothbrush through an aperture 220A-220C associated with the respective guide tube 212A-212C.

Each toothbrush insertion aperture (e.g., 210A) and/or guide tube 212A-212C preferably has an associated marking element (e.g., marking element 211A) providing visible differentiation between the different toothbrush insertion apertures of the device. Such marking elements (e.g., marking element 211A) may differ in terms of color, size, shape, texture, or any combination of the foregoing parameters. Each marking element (e.g., 211A) may be provided in any suitable location proximate to an associated toothbrush aperture (e.g., 210A), such as along outer surface of the base 205, within a guide tube 212A-212C, or both.

The base 205 shown in FIG. 11 is preferably stationary in character, with the bottom surface 201 disposed on or just above an underlying surface such as a countertop. Various methods may be employed to supply oral care capsules to each aperture 220A-220C. In one embodiment, separate ramps (not shown) may be provided to guide oral care capsules from a container (e.g., container 108 shown in FIG. 4) to each aperture 220A-220C, with an optional interposing distribution plate (e.g., distribution plate 141 shown in FIGS. 8-9, optionally modified to include multiple apertures) for regulating passage of oral care capsules. In another embodiment, a single ramp or guide may be employed and selectively moved (e.g., in conjunction with movement of a container 108) into position to supply an oral care capsule to an aperture 220A, 220B, 220C. Such movement may include manual operation by a user, or automated movement with an electric motor (not shown).

In operation of a dispenser including the base portion 205, a first user inserts a portion of a toothbrush (e.g., toothbrush 10 as described hereinabove) into a toothbrush insertion aperture (e.g. insertion aperture 210A) to contact a bristle spreader (e.g., bristle spreader 219A) disposed therein. Each toothbrush insertion aperture shown in FIG. 11 is arranged to receive a toothbrush 10 (as described hereinabove) with bristles facing upward. The bristle spreader (e.g., 219A) has a wedge-shaped leading edge adapted to spread apart angled bristles of the toothbrush 10 to prepare the brush head 20 to receive an oral care capsule. An oral care capsule (not shown) is directed through an oral care capsule loading aperture (e.g., aperture 220A) past spread-apart angled bristles 26A, and into an oral care capsule receiving zone 25 of the brush head 20 of the tooth brush 10. Any various loading mechanism (e.g., mechanically and/or electrically actuated) within the knowledge of one skilled in the art may be used to load a toothbrush with an oral care capsule as described herein. Upon removal of the brush head 20 from the bristle spreader 219A, the angled bristles 26A return to their relaxed position to contract around an oral care capsule disposed within the capsule receiving zone 25. The toothbrush 10 is then removed from the toothbrush insertion aperture 210A, and utilized by the user for oral cleaning.

Second and third users with a different toothbrushes may repeat the foregoing procedure, but each utilizing dedicated toothbrush insertion apertures and guide tubes 210A, 210B, 210C, to prevent contact between different brushes and any single interface surface of the dispenser.

While the invention has been has been described herein in reference to specific aspects, features, and illustrative embodiments of the invention, it will be appreciated that the utility of the invention is not thus limited, but rather extends to and encompasses numerous other variations, modifications, and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A dispensing device configured for use with at least one toothbrush including a brush head having a capsule receiving zone configured to receive an oral care capsule, the dispensing device comprising:

a container including an interior arranged to contain a plurality of oral care capsules including the oral care capsule;

a bristle spreading element including an aperture arranged to permit passage of the oral care capsule, the bristle spreading element arranged to spread apart at least some bristles of the brush head to prepare the brush head to receive the oral care capsule in the capsule receiving zone; and a moveable dispensation element arranged to contact and push the oral care capsule through the aperture to be received by the capsule receiving zone of the brush head.

2. The dispensing device of claim 1, wherein the container comprises a ramp arranged to guide oral care capsules of the plurality of oral care capsules toward the moveable dispensation element.

3. The dispensing device of claim 1, further comprising at least one moveable sealing element arranged to reduce infiltration of moisture into the container between cycles of dispensing oral care capsules of the plurality of oral care capsules from the dispensing device.

4. The dispensing device of claim 1, further comprising a selectively closable dispensing orifice configured to permit dispensation of at least one oral care capsule of the plurality of oral care capsules from the container.

5. The dispensing device of claim 1, further comprising a desiccant material arranged in moisture receiving relationship with the interior of the container.

6. The dispensing device of claim 1, further comprising a guide tube arranged to receive the brush head, wherein the bristle spreading element bounds a portion of the guide tube.

7. The dispensing device of claim 1, wherein the moveable dispensation element comprises at least one of a push bar, an arm, a lever, or a spring.

8. A dispensing device configured for use with at least one toothbrush including a brush head having a capsule receiving zone sized to receive an oral care capsule, the dispensing device comprising:
 a bristle spreading element configured to contact the brush head and spread apart at least some bristles of the brush head to promote passage of the oral care capsule into a retention structure associated with the brush head to enable receipt of said oral care capsule into the capsule receiving zone; and
 at least one dispensation element configured to deliver said oral care capsule through the bristle spreading element into the capsule receiving zone.

9. The dispensing device of claim 8, wherein the bristle spreading element comprises a reduced thickness portion configured to spread apart the at least some bristles of the brush head.

10. The dispensing device of claim 8, further comprising a container containing a plurality of oral care capsules.

11. The dispensing device of claim 8, further comprising a guide tube configured to receive and guide the brush head into position for loading the oral care capsule therein.

12. The dispensing device of claim 8, further comprising:
 a container having an interior configured to contain a plurality of oral care capsules, and
 at least one selectively closable dispensing orifice configured to permit dispensation of at least one oral care capsule of the plurality of oral care capsules from the container.

13. The dispensing device of claim 12, further comprising a desiccant material disposed to receive moisture from the interior.

14. The dispensing device of claim 12, wherein said container comprises at least one ramp configured to guide said plurality of oral care capsules toward said at least one selectively closable dispensing orifice for dispensation of the at least one oral care capsule of the plurality of oral care capsules through the at least one selectively closable dispensing orifice.

15. The dispensing device of claim 12, configured to effectuate automatic dispensation of at least one oral care capsule of the plurality of oral care capsules from the container through the at least one selectively closable dispensing orifice.

16. An oral care capsule dispensing device, comprising:
 a container having an interior configured to contain a plurality of oral care capsules;
 a bristle spreading element configured to contact a brush head and spread apart at least some bristles of the brush head to promote passage of at least one oral care capsule of the plurality of oral care capsules through the bristle spreading element into a retention structure of the brush head; and
 at least one selectively closable dispensing orifice configured to permit dispensation of the at least one oral care capsule from the container.

17. The oral care capsule dispensing device of claim 16, being configured for use with at least one toothbrush including a brush head having a capsule receiving zone sized to receive an oral care capsule of the plurality of oral care capsules, the dispensing device further comprising at least one dispensation element configured to deliver said oral care capsule into the capsule receiving zone.

18. The oral care capsule dispensing device of claim 16, further comprising a desiccant material disposed to receive moisture from the interior.

19. The oral care capsule dispensing device of claim 16, wherein said container comprises at least one ramp configured to guide said plurality of oral care capsules toward said at least one selectively closable dispensing orifice for dispensation of the at least one oral care capsule through the at least one selectively closable dispensing orifice.

20. The oral care capsule dispensing device of claim 16, configured to effectuate automatic dispensation of the at least one oral care capsule from the container through the at least one selectively closable dispensing orifice.

* * * * *